(12) United States Patent
Katzir et al.

(10) Patent No.: US 7,641,365 B2
(45) Date of Patent: Jan. 5, 2010

(54) LINEAR LIGHT CONCENTRATOR

(75) Inventors: Yigal Katzir, Rishon Lezion (IL); Elie Meimoun, Jerusalem (IL)

(73) Assignee: Orbotech Ltd, Yavne (IL)

( * ) Notice: Subject to any disclaimer, the term of this patent is extended or adjusted under 35 U.S.C. 154(b) by 180 days.

(21) Appl. No.: 11/549,200

(22) Filed: Oct. 13, 2006

(65) Prior Publication Data
US 2008/0089052 A1   Apr. 17, 2008

(51) Int. Cl.
*F21V 5/00* (2006.01)
(52) U.S. Cl. .................. 362/327; 362/326; 362/329; 362/334; 362/335; 362/340; 359/708; 359/711; 359/712
(58) Field of Classification Search .................. 362/559, 362/560, 326–640, 268, 336, 338, 335, 308; 362/310, 311.06, 311.14, 245; 359/708, 359/711, 712, 710, 719
See application file for complete search history.

(56) References Cited

U.S. PATENT DOCUMENTS

| 2,254,962 | A | * | 9/1941 | Bitner et al. ................ 362/327 |
|---|---|---|---|---|
| 5,032,960 | A | * | 7/1991 | Katoh ........................ 362/240 |
| 5,103,381 | A | | 4/1992 | Uke |
| 5,526,190 | A | * | 6/1996 | Hubble et al. ............... 359/719 |
| 5,745,176 | A | | 4/1998 | Lebens |
| 6,619,831 | B2 | * | 9/2003 | Kanesaka ................... 362/555 |
| 6,827,467 | B2 | * | 12/2004 | Tenmyo ...................... 362/268 |
| 7,213,945 | B2 | * | 5/2007 | Yoneda et al. .............. 362/309 |
| 2003/0156414 | A1 | * | 8/2003 | Tenmyo ...................... 362/268 |

* cited by examiner

*Primary Examiner*—Sandra L O'Shea
*Assistant Examiner*—Evan Dzierzynski
(74) *Attorney, Agent, or Firm*—Sughrue Mion, PLLC

(57) ABSTRACT

An optical element including a unitary, non-circularly-symmetrical, piece of optically-transmissive material, which has at least first and second surfaces for concentrating light from a light source onto a linear target region, such that at least one of the first and second surfaces is curved, and such that a first portion of the light is concentrated onto the linear target region by reflection from the first surface, while a second portion of the light is concentrated onto the linear target region by refraction at the second surface.

30 Claims, 10 Drawing Sheets

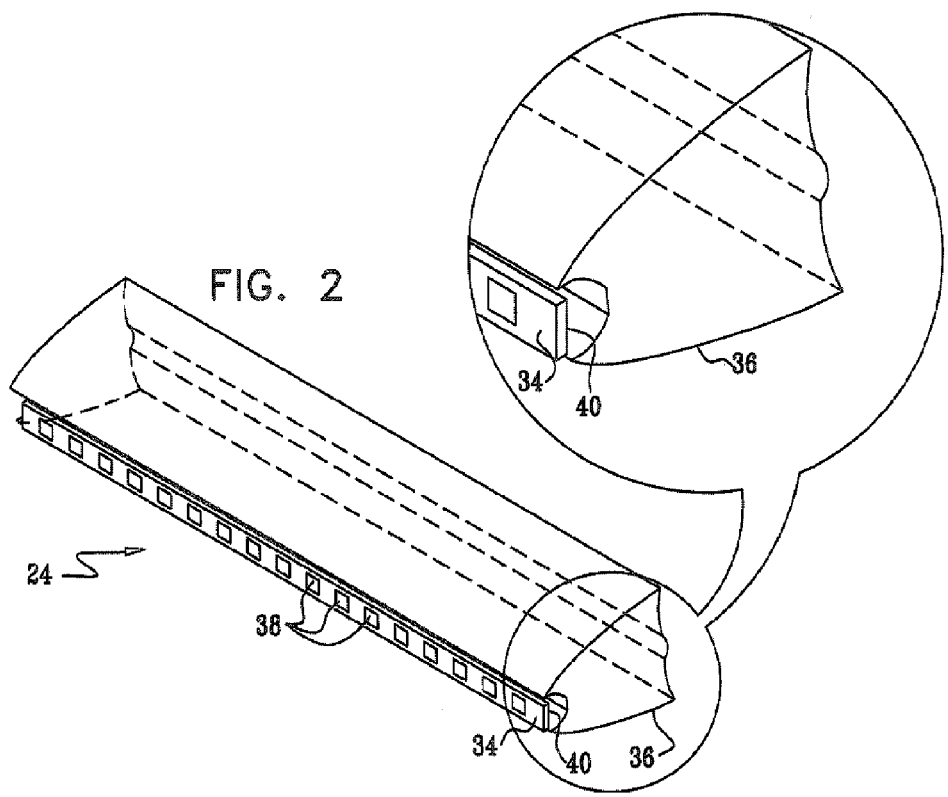
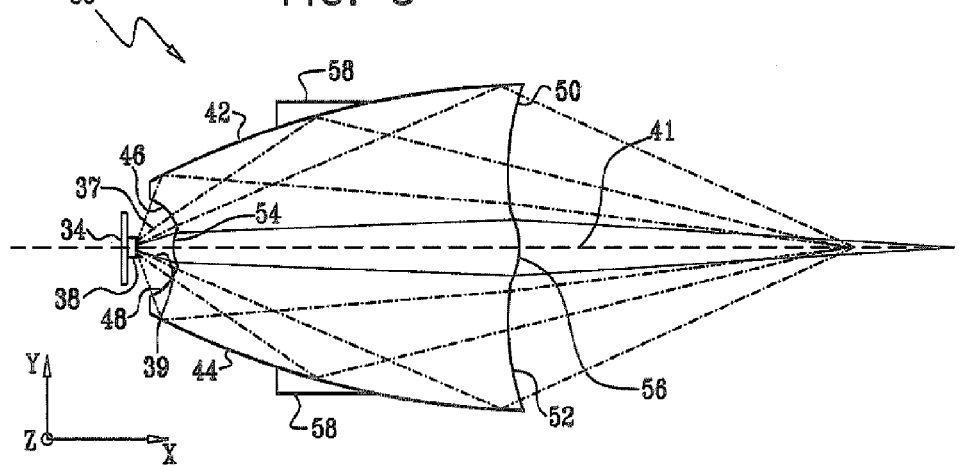

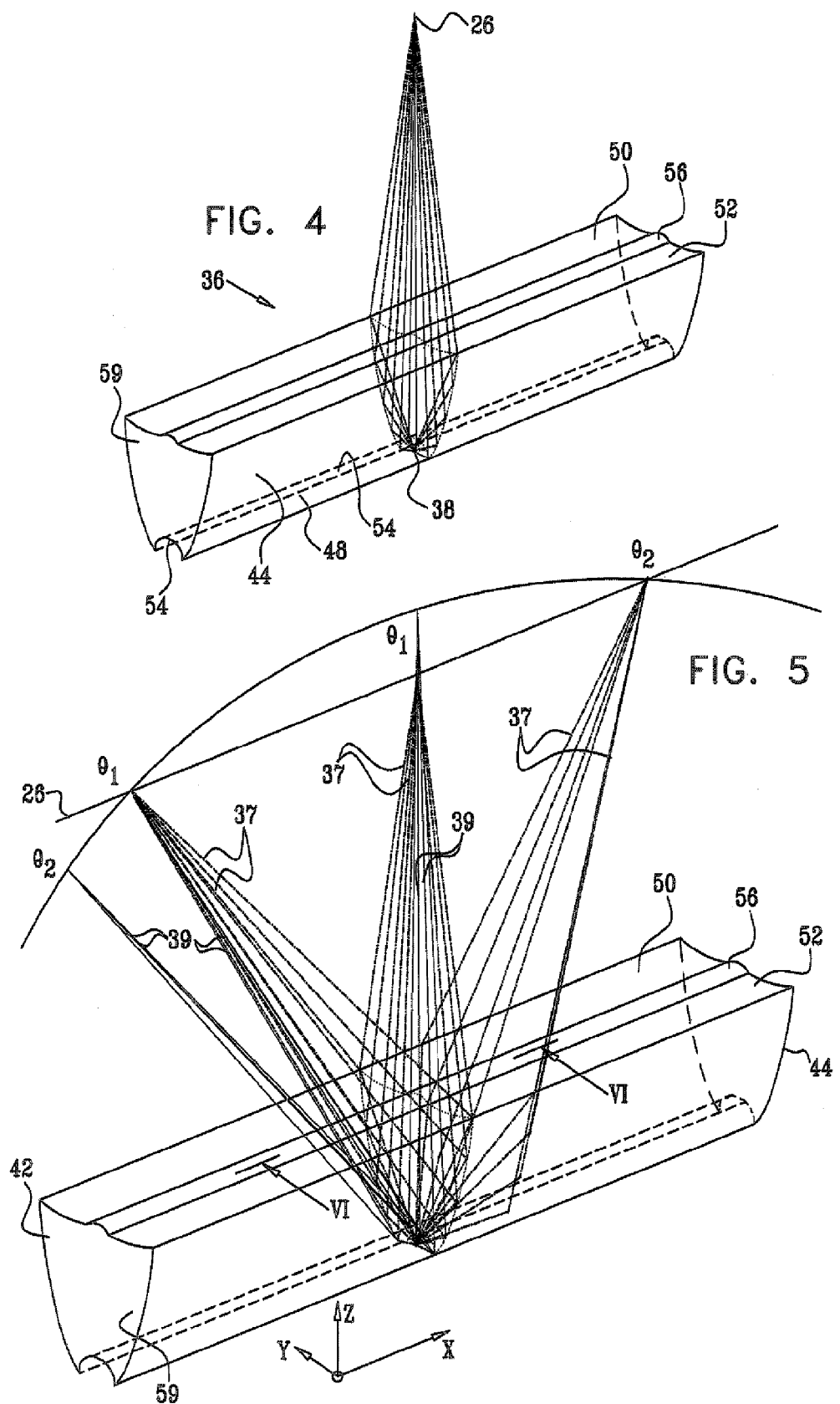

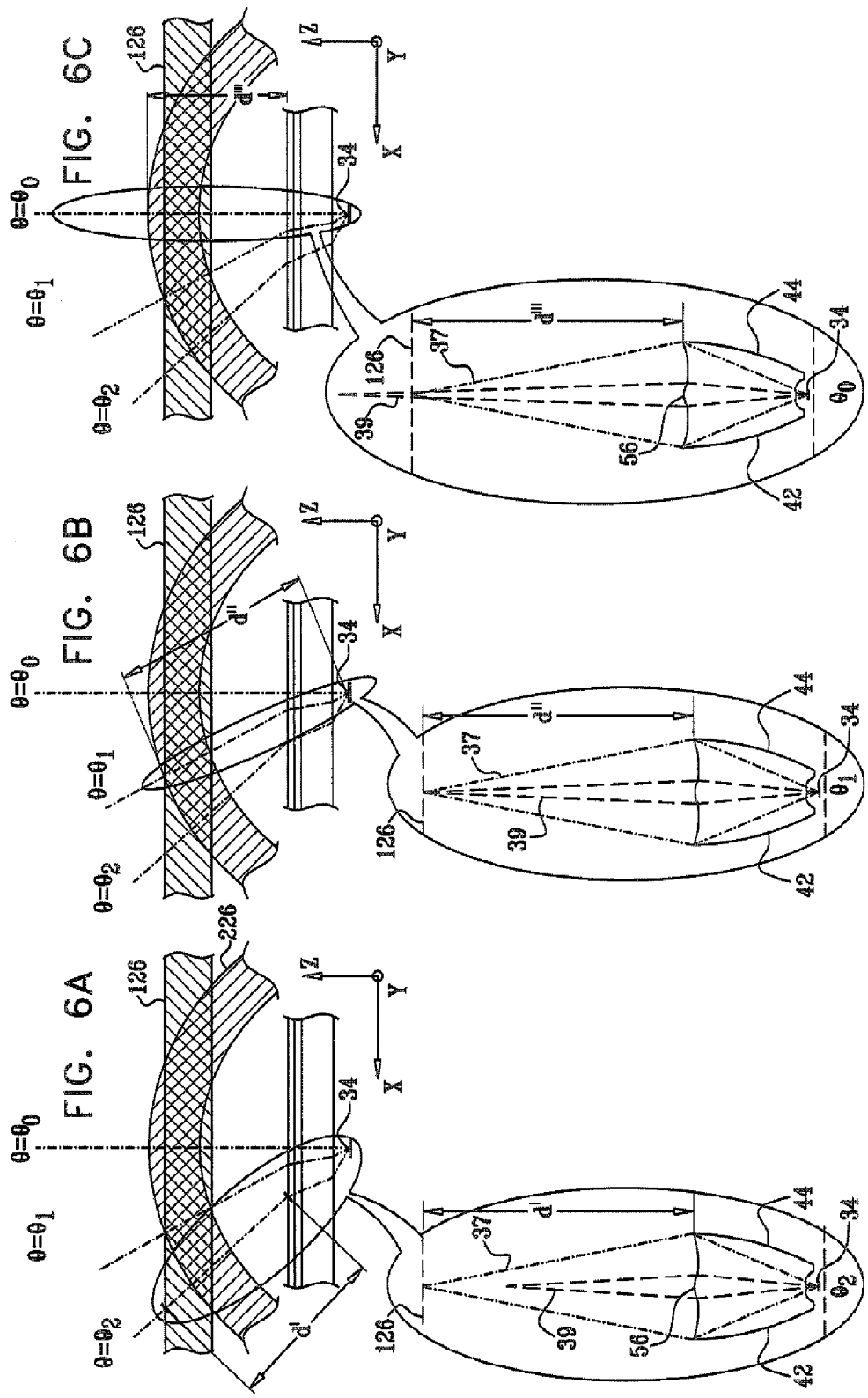

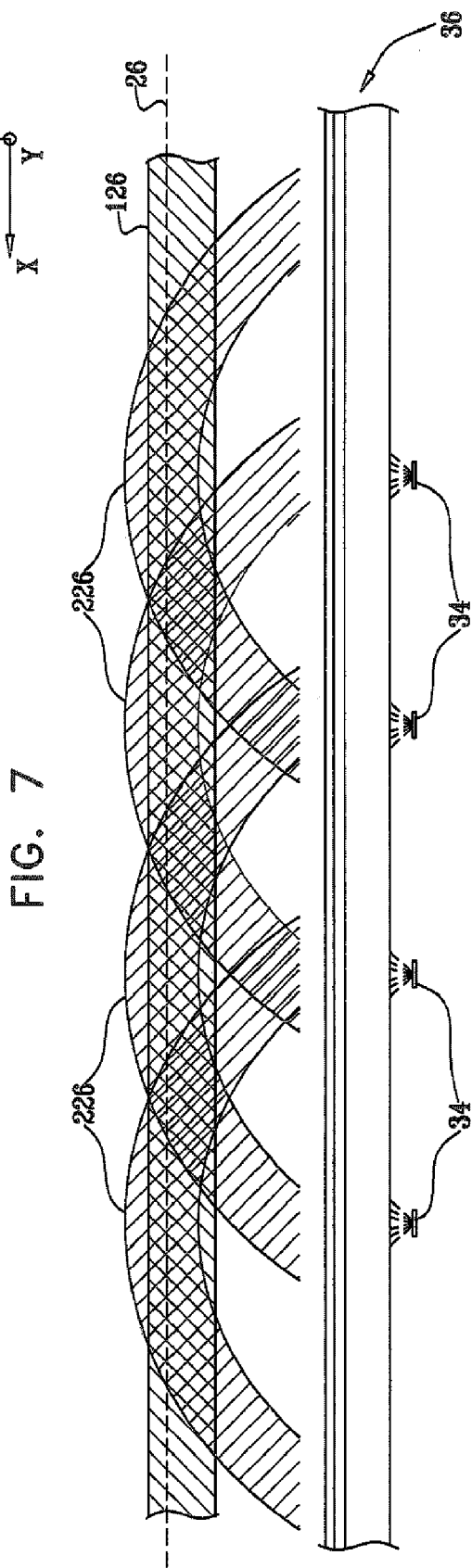

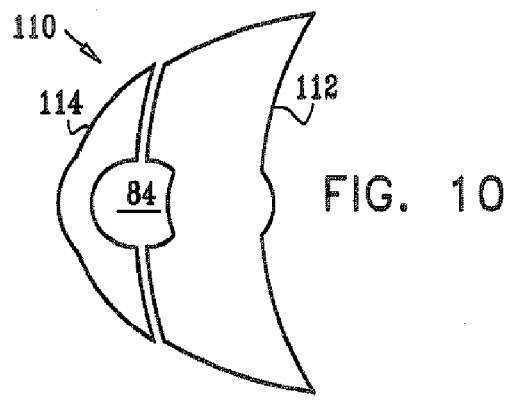
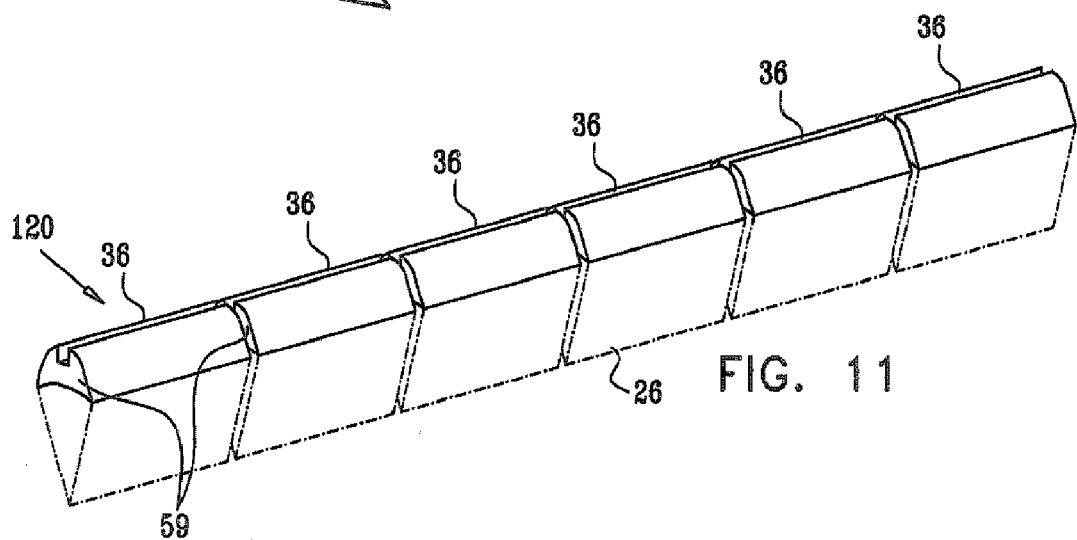
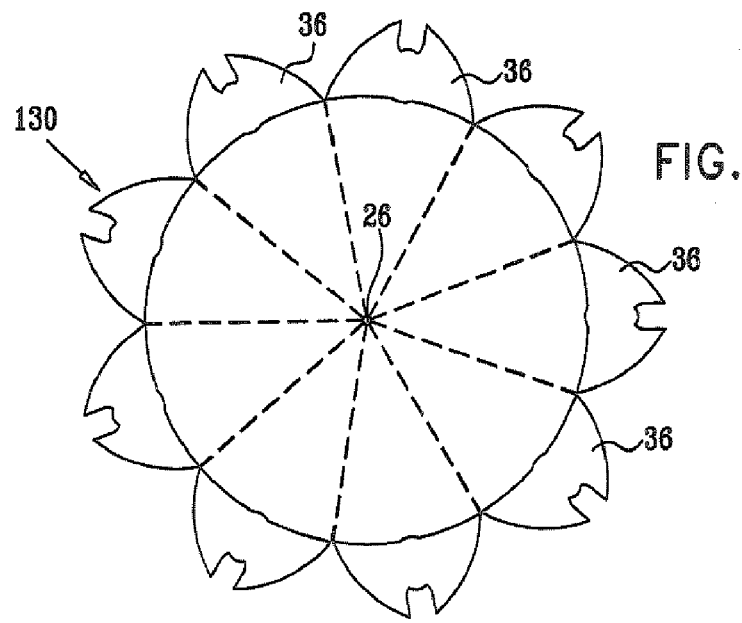

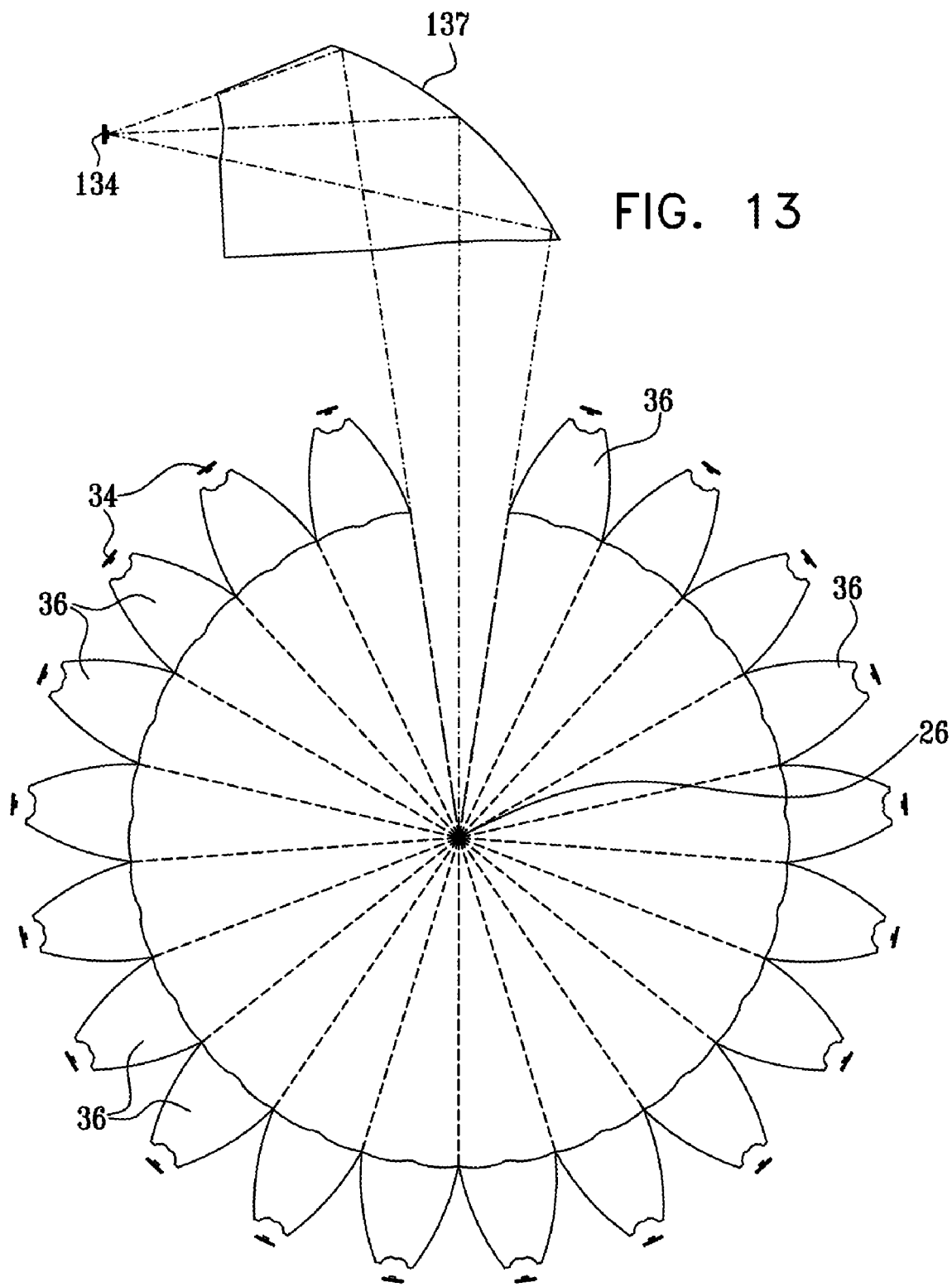

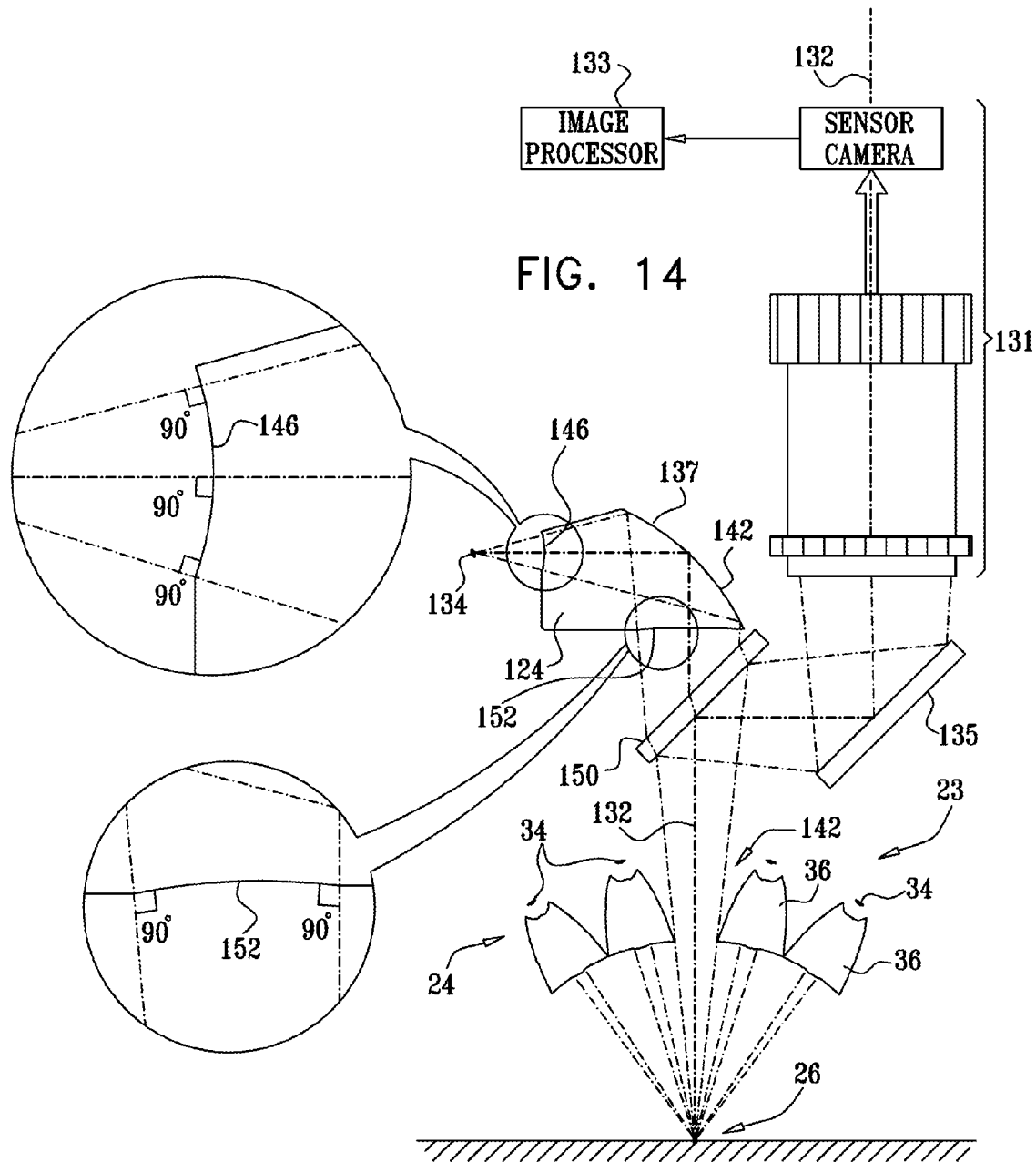

LINEAR LIGHT CONCENTRATOR

FIELD OF THE INVENTION

The present invention relates generally to light concentrators, and specifically to optics for concentrating light from a multi-directional source onto a linear target region.

BACKGROUND OF THE INVENTION

Various types of optical systems are known in the art for concentrating light from a linear source onto a linear target region. Considerable research and design resources have been invested in developing highly efficient light sources, including for example diodes, that constitute compact extended sources which emit multi-directional light from a nearly point location, however conventional optical components are not optimal for concentrating light from such compact extended sources onto a linear target region.

SUMMARY OF THE INVENTION

Embodiments of the present invention provide a novel optical element suitable for concentrating light from a light source onto a linear target region. Such elements comprise both reflective and refractive surfaces, which are arranged to concentrate different portions of the light emitted from the source in a different manner. The elements provide relatively high collection angles and relatively low levels of aberration, leading to high efficiency and accuracy of light collection and concentration onto the linear target region. Although an optical element as described hereinbelow is particularly suitable for use in conjunction with compact extended light sources, such as LEDs, it may also be adapted for use with other extended light sources as well, such as filament lamps for example.

These novel optical elements may be used in a variety of applications. In some embodiments, one or more elements of this sort are used to illuminate a linear region in a scanning optical inspection system, in conjunction with a detector array, which captures the light that is reflected from the illuminated region, or that passes through the illuminated region, for example from backlighting, and which outputs a signal representative of the being inspected to a processor for processing, for example to determine the presence of defects in the object. As used herein, the term reflected includes, without limitation, light that is specularly reflected or diffusively reflected (scattered) from an illuminated surface.

The present invention will be more fully understood from the following detailed description of the embodiments thereof, taken together with the drawings in which:

BRIEF DESCRIPTION OF THE DRAWINGS

FIG. 2 is a schematic, pictorial illustration of a linear illumination unit, in accordance with an embodiment of the present invention;

FIG. 3 is a schematic, sectional view of a light concentrator, showing a ray trace, in accordance with an embodiment of the present invention;

FIG. 4 is a schematic, isometric view of the light concentrator of FIG. 3, showing a ray trace in a sagittal plane, for a perpendicular tangential direction, in accordance with an embodiment of the present invention;

FIG. 5 is a schematic, isometric view of the light concentrator of FIG. 3, showing ray traces in a sagittal plane for several different tangential directions, in accordance with an embodiment of the present invention;

FIGS. 6a-6c are schematic side views of a light concentrator, showing a projection for illumination rays for different selected tangential angles, in accordance with an embodiment of the present invention;

FIG. 7 is a schematic side view of a light concentrator showing overlapping illumination regions for several compact extended light emitters, in accordance with an embodiment of the invention;

FIG. 10 is a schematic, sectional view of a light concentrator, in accordance with another embodiment of the present invention;

FIG. 11 is a schematic, pictorial illustration of a light concentration assembly, in accordance with an embodiment of the present invention; and FIG. 12 is a schematic, sectional view of a light concentration assembly, in accordance with another embodiment of the present invention;

FIG. 13 is a schematic, sectional view of a light concentration assembly, in accordance with still another embodiment of the present invention;

FIG. 14 is a simplified side view illustration of an image acquisition assembly, in accordance with an embodiment of the invention;

DETAILED DESCRIPTION OF EMBODIMENTS

Figure 1A:
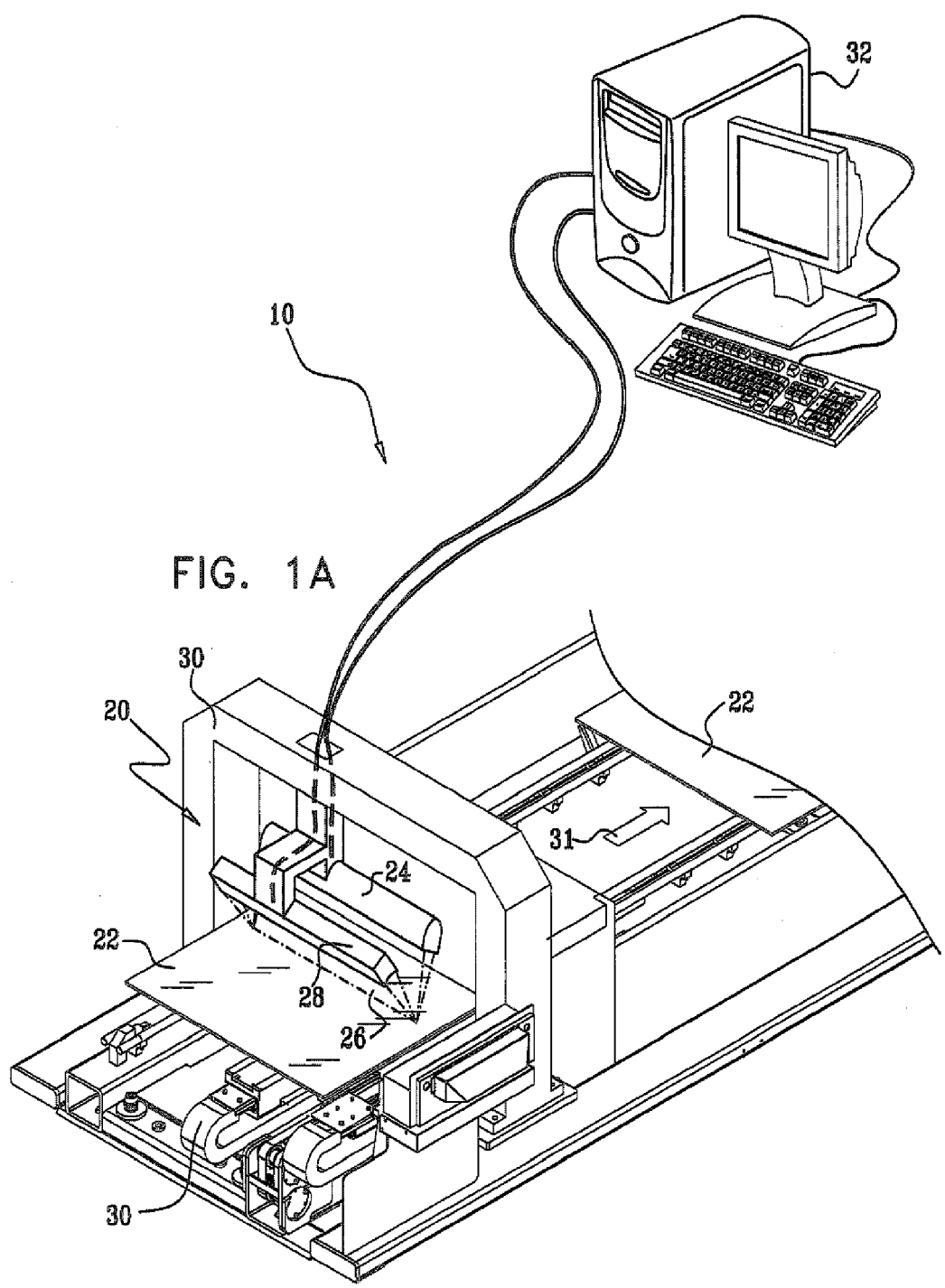
FIG. 1a is a highly simplified schematic, pictorial illustration of a system for automated optical inspection of planar substrates, in accordance with an embodiment of the present invention.

FIG. 1a is a highly simplified, schematic, pictorial illustration of a system 10 for automated optical inspection of an object 22, in accordance with an embodiment of the present invention. Object 22 typically comprises a generally planar structure having a patterned formation thereon, including without limitation a bare printed circuit board, a populated printed circuit board, a flat panel display or a semiconductor wafer, for example. At least one linear illumination unit 24 illuminates a linear target region 26 on the surface of object 22. The term target region, as used in this description and in the claims below includes both target regions which are an actual physical illuminated area on a surface, as shown in FIGS. 1A and 1B inter alia, as well as aerial illumination regions defining a linear light source that is suspended in space which may be employed, for example, as an input for auxiliary illumination optics such as downstream cylindrical lenses or elliptically cylindrical reflectors.

Illumination unit 24 is described in detail with reference to the figures that follow. A detection unit 28 captures an image of region 26. Typically, detection unit 28 comprises one or more rows of optical detectors with suitable image acquisition optics (not shown) for focusing light reflected from region 26 onto the detectors, as is known in the art. Optionally illumination of region 26 may be provided, additionally or alternatively, by transmitted light that is provided by backlighting (not seen in FIG. 1a).

A motion assembly 30 translates object 22 in a direction indicated by arrow 31 so that the target region 26 is scanned over the entire area of interest on the surface of the object (wherein the area of interest may comprise all or only a part of the surface). Alternatively or additionally, the motion assembly may scan the target region by translating illumination unit 24 and detection unit 28. A computer controller 32, which includes image processing circuitry, controls the elements of system 10 and receives and processes electronic image signals generated by detection unit 28. The image processor is thus able, for example, to combine the successive images formed by detection unit into a complete two-dimensional image of the area of interest, as well as to analyze the images in order to detect defects and otherwise inspect the surface of the object.

Figure 1B:
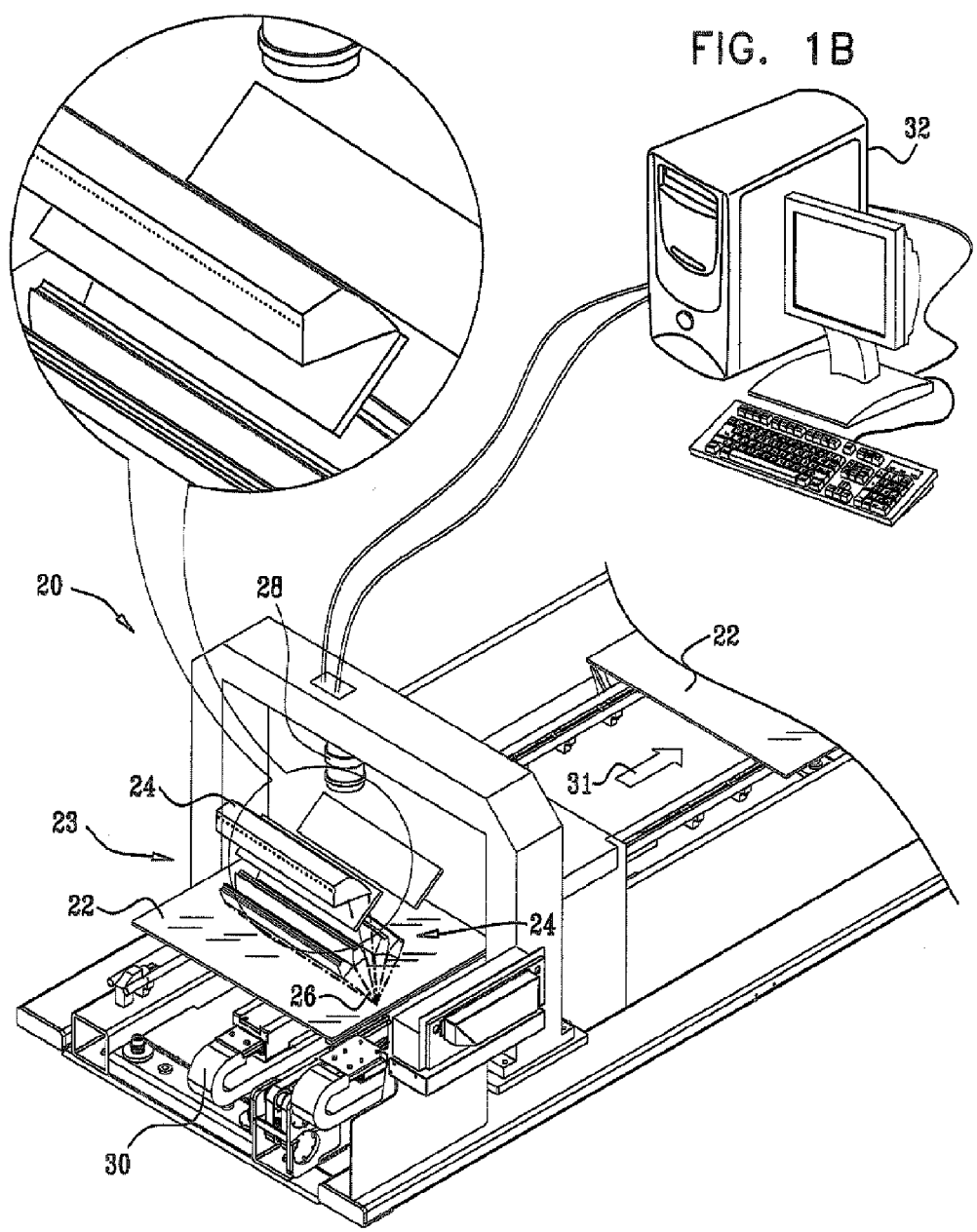
FIG. 1b is a highly simplified schematic, pictorial illustration of a system for automated optical inspection of planar substrates, in accordance with another embodiment of the present invention.

FIG. 1b is a highly simplified, schematic, pictorial illustration of a system 20 for automated optical inspection of an object 22, in accordance with another embodiment of the present invention. Object 22 typically comprises a generally planar structure having a patterned formation thereon, such as a printed circuit board or semiconductor wafer, for example. An image acquisition assembly 23 comprising a plurality of linear illumination units 24, illuminates a linear target region 26 on the surface of object 22 to acquire an image thereof.

Image acquisition assembly 23 and illumination unit 24 are described in detail with reference to the figures that follow. A detection unit 28 captures an image of region 26. Typically, detection unit 28 comprises one or more rows of optical detectors with suitable image acquisition optics (not shown) for focusing light reflected from region 26 onto the detectors, as is known in the art. Optionally illumination of region 26 may be provided, additionally or alternatively, by transmitted light that is provided by backlighting (not shown).

A motion assembly 30 translates object 22 in a direction indicated by arrow 31 so that the target region is scanned over the entire area of interest on the surface of the object (wherein the area of interest may comprise all or only a part of the surface). Alternatively or additionally, the motion assembly may scan the target region by translating image acquisition assembly 23. A computer controller 32, which includes image processing circuitry, controls the elements of system 20 and receives and processes electronic image signals generated by detection unit 28. The image processor is thus able, for example, to combine the successive images formed by detection unit into a complete two-dimensional image of the area of interest, as well as to analyze the images in order to detect defects and otherwise inspect the surface of the object. Thus, for example, Discovery™ automated optical inspection systems, available from Orbotech Ltd. of Yavne, Israel, may be suitably adapted to incorporate illumination and image acquisition systems described herein in greater detail.

FIG. 2 is a schematic, pictorial illustration of an illumination unit 24, in accordance with an embodiment of the present invention. The illumination unit comprises at least one light source 34 and a unitary light concentrator 36. The light source 34 may comprise a continuous light source, such as a filament emitter, or a plurality of compact extended sources such as a plurality of LEDs which may or may not be in mutual contact, for example.

In the context of the present patent application and in the claims, the term "unitary" includes an optical element comprising a single piece of optical material or an optical element comprising a plurality of pieces of an optical material that adjoin one another, as opposed to conventional compound optics having spaces between the elements as are more commonly used when high optical performance is required. Concentrator 36 is not circularly symmetrical. Rather, in this embodiment and in the other embodiments described hereinbelow, the concentrator has a plane of symmetry (corresponding to axis 41 seen in FIG. 3), which passes through light source 34 and through the target region. The longitudinal axis of the light source is parallel to that of the target region. Unitary elements of the type shown in FIG. 2 are advantageous, inter alia, in that they may be manufactured inexpensively by extrusion or drawing, as well as by molding techniques, using for example optical glass, plastics or other suitable light transmissive materials. Other features and advantages of concentrator 36 are described with reference to the figures that follow.

In the embodiment shown in FIG. 2, light source 34 comprises an array of light-emitting diodes (LEDs) 38, which are typically provided as individual chips for mounting on a circuit board 40. In an embodiment of the invention LEDs 38 are covered, for example, with a light transmissive encapsulation having a thickness of about 1 mm and a refractive index of 1.45, although non-encapsulated LEDs may also be suitable. In an embodiment of the invention, each LED 38 emits a beam of generally uniform brightness into nearly $2\pi$ steradians.

Alternatively, concentrator 36 and the other types of concentrators described hereinbelow may be used with light sources of other types, particularly linear light sources, such as discharge lamps, linear incandescent filaments, fluorescent tubes, and other sorts of emitters that are known in the art. The terms "light" and "illumination" are used in the current disclosure and in the claims to denote any and all radiation in the optical range, which is defined as including not only visible light, but also light in the infrared and ultraviolet wavelength ranges that can be concentrated by transmissive elements made of suitable materials.

Reference is now made to FIGS. 3 and 4, wherein FIG. 3 is a schematic, sectional illustration of concentrator 36, showing a ray trace, while FIG. 4 is an isometric view of concentrator 36 showing a ray trace for an elemental LED 38 of light source 34 in the sagittal plane of concentrator 36, for a perpendicular tangential direction. One portion of the light from light source 34, comprising relatively high angle rays 37 emitted at high angles relative to plane of symmetry 41 of the concentrator 36 (i.e., the X-Z plane in this illustration), enters the concentrator 36 through entry surfaces 46 and 48 and then reflects off aspheric reflective surfaces 42 and 44, for example, by total internal reflection, although this need not be the case, and subsequently exits through exit surfaces 50 and 52 respectively to impinge on target region 26 (FIGS. 1A and 1B). In an embodiment of the invention aspheric reflective surfaces 42 and 44 are curved and have a non-parabolic section.

Thus, in embodiments where the concentrator 36 is structured such that light from light source 34 is reflected at surfaces 42 and 44 by total internal reflection, there is no need to add an external reflective coating to surfaces 42 and 44 respectively, thereby reducing production complexity and fabrication costs. However in some embodiments the addition of a suitable reflective coating to surfaces 42 and 44, such as a silver reflective coating, may be necessary or desirable.

Surfaces 46, 48, 50 and 52 are structured and arranged relative to light source 34 to minimize various optical aberrations, including chromatic and a tangential field aberration for an elemental compact extended source, as will be described in greater detail hereinbelow. In accordance with an embodiment of the invention, light enters concentrator 36 through surfaces 46 and 48 at angles generally normal thereto in a perpendicular tangential direction, and light reflected by surfaces 42 and 44 exits concentrator 36 through exit surfaces 50 and 52 at angles generally normal to these surfaces in a perpendicular tangential direction. It is noted that because light source 34 is a compact extended source, and not a perfect point source, not all light emitted therefrom will impinge on surfaces 46, 48, 50 and 52 at angles precisely normal to the respective surface in a perpendicular tangential direction; small deviations from the normal are expected, and suitable design of surfaces 46, 48, 50 and 52 takes these deviations into account.

Another portion of the light from light source 34, comprising low angle rays 39 emitted at relatively low angles relative to plane 41 in the perpendicular tangential direction, enters the concentrator through a collecting surface 54, which directs the rays toward an exit surface 56. These low angle rays 39 are then concentrated onto target region 26 by refraction at exit surface 56. It is noted that in accordance with an embodiment of the invention, the optical surfaces of concentrator 36 are configured and arranged so that low angle rays 39 emitted at a perpendicular tangential direction, converge at a location that is more distant from light source 34 than the location at which high angle rays 37 emitted at a perpendicular tangential direction converge, although this arrangement need not be the case.

Thus, concentrator 36 collects and concentrates the rays emitted from light source 34 up to nearly a full 180° in the sagittal plane, in an embodiment of the invention about 140° in the sagittal plane, with almost no "wasted" rays. Some of the rays emitted by light source 34 (high angle rays 37) are concentrated onto target region 26 by reflection at surfaces 42 and 44, while other rays emitted by light source 34 (low angle rays 39) are concentrated onto target region 26 by refraction through exit surface 56.

It is noted that inasmuch as light source 38 is not an infinitely small point source, correspondingly light therefrom can not be concentrated or focused to an infinitely small location. Thus a finite region of concentrated light having a maximal irradiance will be formed for each LED 38. The width of the focused region, namely the regions having maximal irradiance, is given approximately by the formula: (focal region width)=(source width)×(effective angle of illumination entering the optics)/(effective angle of illumination impinging on the illuminating region).

The design of concentrator 36 is optimized so as to minimize various optical aberrations in the sagittal plane while taking into account the optical size of the source. Thus, for example, the surfaces 54 and 56, which in essence form a cylindrical lens, are configured to reduce tangential field curvature along target region 26 for light emitted by each elemental compact extended light source 34. Moreover, sagittal aberration associated with rays reflected by surfaces 42 and 44 is reduced, for example, by selecting a shape for entry surfaces 46 and 48, and for exit surfaces 50 and 52 such that in the sagittal plane, rays impinging on these surfaces impinge at an angle that is generally normal thereto.

Thus, in an embodiment of the invention, entry surfaces 46 and 48 have approximately cylindrical profiles, generally centered on the optical location of light source 34, so that light enters the concentrator at close to a normal sagittal angle of incidence and thus undergoes minimal aberration at these surfaces. Similarly, exit surfaces 50 and 52 are suitably curved so that light exits the concentrator 36 at an angle nearly normal to these surfaces in the sagittal plane. Thus, sagittal aberration due to refraction at surfaces 46, 48, 50 and 52 is minimized. Reflective surfaces 42 and 44, inherently do not introduce chromatic or field curvature aberrations and may be designed to minimize other aberrations given the actual dimensions of the light-emitting area of light source 34.

Reference is made to FIG. 5 which is a schematic, isometric view of concentrator 36 showing ray traces in four different tangential directions, in accordance with an embodiment of the present invention, to FIGS. 6A-6C which are schematic side views of a light concentrator, showing a projection for illumination rays for three selected tangential angles, in accordance with an embodiment of the present invention, and to FIG. 7 which is a schematic side view of a light concentrator showing overlapping illumination regions for several compact extended light emitters, in accordance with an embodiment of the invention.

High angle light rays 37 emitted from a given elemental source 34 and reflected by either of surfaces 42 and 44 converge to target region 26 at a generally constant distance, regardless of the tangential angle $\theta$. Due to the extended nature of source 34, reflected rays illuminate a rectilinear illumination region 126. However, low angle light rays 39 emitted from a given elemental source 34 and refracted at surface 56 converge near target region 26 but at distance therefrom that is a function of the tangential angle, to illuminate a curved illumination region 226. In accordance with an embodiment of the invention, ends 59 of each concentrator reflect tangential rays impinging thereon to redirect these rays to illuminated region 26. Reflection may be due to total internal reflection. Optionally surfaces may be suitably coated with a reflective coating.

As illustrated in FIG. 7, when illumination is provided by a plurality of spatially separated elemental sources 34, there is substantially no field curvature over the entire target region 26 for light reflected by surfaces 42 and 44, as shown by rectilinear illumination region 126 enveloping target region 26, even though the sources are spatially separated. Although the illumination field 226 for light refracted by surface 56 is curved for each elemental source 34, suitable design of concentrator 36, and spacing of sources 34, produce a plurality of overlapping curved illumination fields 226. The combination of rectilinear illumination field 126 and the plurality of curved illumination fields 226, produced by concentrator 36 and suitably spaced apart compact extended light sources configured in accordance with an embodiment of the invention, thus generally substantially uniformly illuminates surface 26 within a solid angle of illumination.

It is noted that rays emitted from source 34, including rays that are reflected by surfaces 42 and 44, at large tangential angles will experience tangential chromatic aberration due to refraction at the entry and exit surfaces of concentrator 36. However, in an embodiment of the invention employing multiple sources 34, each source 34 illuminating overlapping regions, chromatic dispersion will tend to average out, so that the color and intensity of the illumination will be approximately constant over nearly the entire length of target region 26.

Said another way, in accordance with an embodiment of the invention as described above, the curves of refracting surfaces 46, 48, 50 and 52 are selected such that paths of light beginning at light source 34, pass through entry surfaces 46 or 48, are reflected by surfaces 42 or 44, and then are refracted again by surfaces 50 or 52, with the surfaces 46, 48, 50 and 52 being configured and arranged to intrinsically minimize sagittal aberrations. However, surfaces 54 and 56, which generally act as a cylindrical lens, cause light emitted by each light source 34 and passing through these surfaces to be focused onto a region that is curved in the tangential plane. In accordance with an embodiment of the invention, the plurality of light sources thus generates a plurality of overlapping curved illumination regions.

Because of the design features described above, the performance of concentrator 36 has little sensitivity to wavelength or to the refractive index of the material from which the concentrator is made. Consequently, the concentrator may be made from a wide range of materials and used over a wide range of wavelengths. Because the reflective surfaces of the concentrator operate by total internal reflection, the concentrator may be made from materials that are not amenable to coating, such as Zeonex.

In accordance with embodiments of the invention, concentrator 36 may be produced by injection molding or by extrusion processes, and includes mounting stubs 58 for use in mounting the concentrator in a housing. In an embodiment of the invention, mounting stubs 58 are discrete elements that are positioned, so as to minimize their effect on reflective properties of concentrator 36. A typical concentrator 36, suitable for use in conjunction with an emitter comprising a plurality of compact extended sources, such as LEDs, has a height of 16.108 mm (in the Z-direction—horizontal in FIG. 3) and a width of 13.892 mm (in the Y-direction). Collecting surface 54 is located 3.000 mm above the front surface of LEDs 38 and has a diameter of 1.900 mm. Exit surface 56 has a width of 3.902 mm. The concentrator can be made or cut to any desired length (wherein the length is the dimension in the X-direction—into the page in FIG. 3), for example, 100-200 mm. Assuming LEDs 38 to have a width of about 1.0 mm, target region 26 produced by concentrator 36 will have a width of greater than 2.0 mm at a distance of 40 mm from the front surface of the concentrator. Further details of the design of concentrator 36 in this embodiment are listed in the Appendix below.

Figure 8:
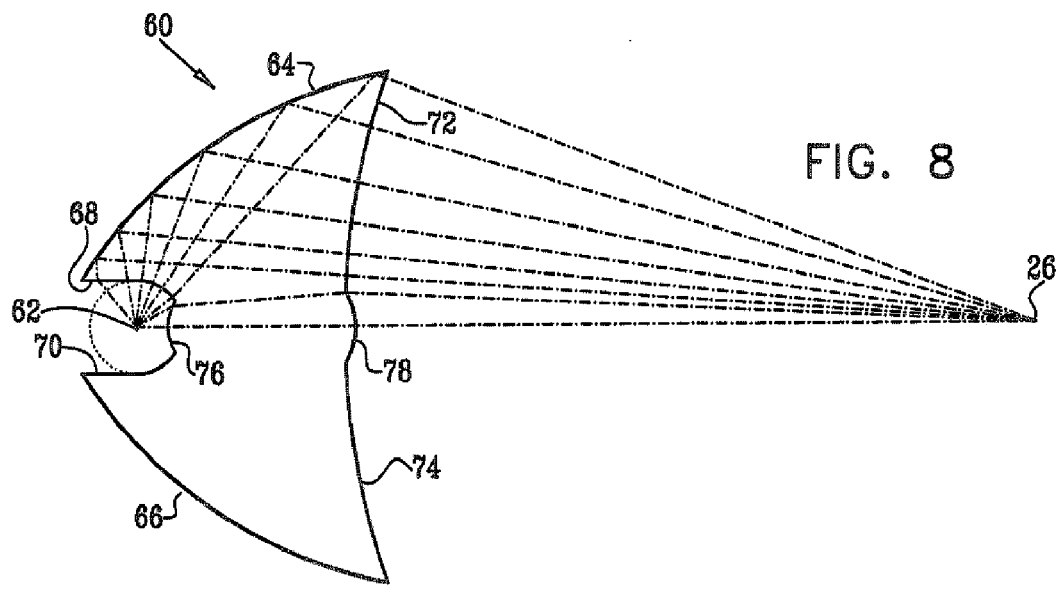
FIGS. 8 and 9 are schematic, sectional views of light concentrators, including ray traces in respective sagittal planes, in accordance with alternative embodiments of the present invention.

Reference is made to FIG. 8 which is a schematic, sectional illustration of a concentrator 60 used with a linear light source 62, in accordance with another embodiment of the present invention. The principles of this embodiment are similar to those of concentrator 36, as described above, i.e., concentrator 60 is non-circularly-symmetrical and has a plane of symmetry passing through source 62 and target region 26, perpendicular to the page of the drawing. Concentrator 60, however, is configured to collect and focus light from source 62 over a larger angle in the sagittal plane, in this case approximately 270°. This embodiment is useful, for example, when source 62 comprises a filament, discharge arc, or fluorescent source, which emits light over a range of angles larger than 180° in the sagittal direction.

Rays emitted from source 62 at high angles (up to ±135°) enter concentrator 60 through entrance surfaces 68 and 70 and are reflected toward target region 26 by internal reflection from reflecting surfaces 64 and 66. A reflective coating is typically applied to at least a part of surfaces 64 and 66, for example to those portions of the outside of surfaces 64 and 66 where the angle of incidence of some of the rays on the surface may be too small for total internal reflection. The rays reflected from surfaces 64 and 66 exit concentrator 60 through exit surfaces 72 and 74 which are configured to minimize sagittal aberrations, for example as described hereinabove with reference to FIG. 3. Rays emitted from light source 62 at low angles are focused onto target region 26 by refraction at a collecting surface 76 and an exit surface 78. Such configuration can be manufactured by plastics molding (subject to implementation of suitable draft angles to facilitate extraction of the concentrator from the mold) or extrusion processes, for example.

Figure 9:
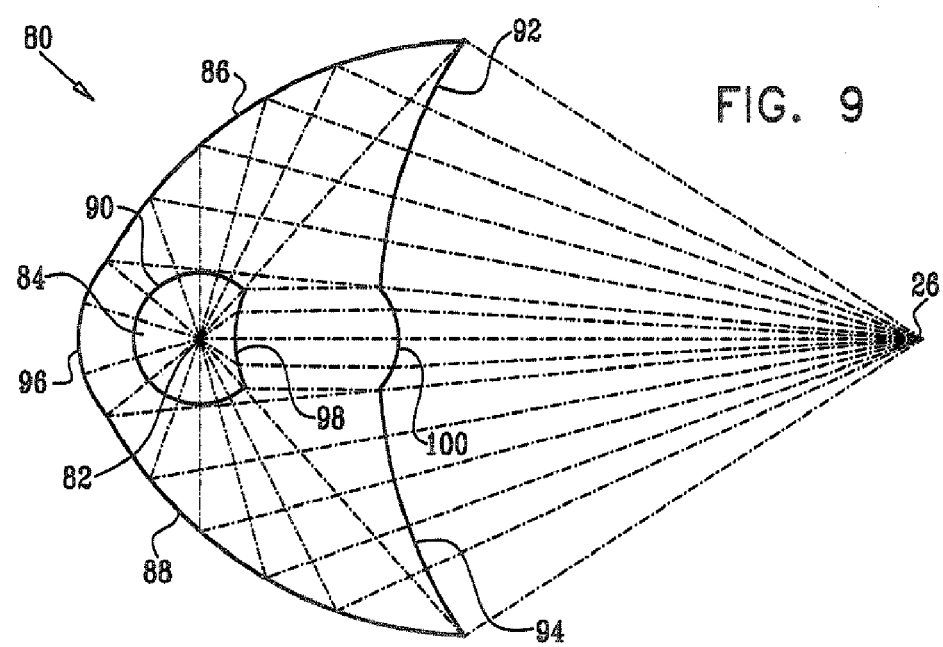

Reference is made to FIG. 9 which is a schematic, sectional illustration of a concentrator 80 for use with a linear light source 82, in accordance with yet another embodiment of the present invention. As in the preceding embodiments, concentrator 80 is non-circularly-symmetrical and has a horizontal plane of symmetry relative to the page of the drawing. Concentrator 80 is configured to collect and focus light from source 82 over 4π steradians. Thus, when a source such as a filament, arc, or fluorescent tube is used, concentrator 80 collects and focuses nearly all the light generated by the source.

Source 82 is contained inside a cavity 84 within concentrator 80. Rays emitted from the source at high angles (up to ±180°) pass into the concentrator through a cylindrical entry surface 90. Since surface 90 has a circular profile, centered on light source 82, the rays are not refracted at surface 90, and thus sagittal aberration is generally not induced. Rays in the lower portion of the high angular range reflect from reflective surfaces 86 and 88, which concentrate the rays through exit surfaces 92 and 94 onto target region 26. Rays in the higher portion of the high angular range are reflected back toward the location of light source 82 by a rear reflective surface 96. Typically, surface 96 also has a circular profile centered on light source 82. Reflective coatings are typically applied to surfaces 86, 88 and 96. The rays reflected from surface 96, as well as the rays emitted from source 82 at low angles, are focused onto target region 26 by refraction at a collection surface 98 and an exit surface 100. Alternatively, a reflective coating may be applied to a portion of surface 90, thus obviating the reflective function of surface 96.

FIG. 10 is an exploded schematic, sectional illustration of a concentrator 110, in accordance with yet another embodiment of the present invention. Concentrator 110 operates on the same principles as concentrator 80, as shown in FIG. 9, but is designed for greater ease of manufacture. Concentrator 110 is constructed from a front piece 112 and a rear piece 114, which are manufactured separately by injection molding or extrusion, for example. The two pieces are then glued together using a suitable optical cement or placed in close proximity to each other.

FIG. 11 is a schematic, pictorial illustration of a light concentration assembly 120, in accordance with an embodiment of the present invention. Assembly 120 comprises multiple concentrators 36 stacked end-to-end, as shown in the figure. (Alternatively, other types of concentrators based on the principles of the present invention, such as those shown in FIGS. 8-10, may be combined in this manner, as well as in the manner shown in FIG. 12 below, or both.) This configuration permits a more extended target region 26 to be illuminated. Tangential rays striking the end 59 of a given concentrator are reflected back into the concentrator by way of total internal reflection. Optionally a suitable reflective coating is provided. Such reflection effectively reduces the loss of light emitted by the light sources 34.

FIG. 12 is a schematic, sectional illustration of a light concentration assembly 130 in accordance with another embodiment of the present invention. In this embodiment, concentrators 36 are held side-by-side so that multiple concentrators illuminate different portions along the same target region 26. Although in FIG. 12 the target region 26 is illuminated from all sides, a smaller number of concentrators may be used to illuminate the region over a smaller range of sagittal angles. For example, three concentrators could be used together in the configuration of FIG. 12 in order to illuminate the region with light converging over a range of 120° sagittally, without dead zones between units. Multiple concentrator assemblies of the type shown in FIG. 12 may be stacked end-to-end in the manner shown in FIG. 11. Moreover, when arranging an illuminator in the manner shown in FIG. 12, control over a solid angle of illumination employed to illuminate a surface may be achieved so as to optimally adapt illumination for an illumination application.

FIG. 13 is a schematic, sectional illustration of a light concentration assembly 140 in accordance with still another embodiment of the present invention. In this embodiment, concentrators 36 are held side-by-side so that multiple concentrators illuminate different portions along the same target region 26, in a manner similar to that shown in FIG. 12. One of the concentrators 137 is configured to illuminate a region between two concentrators 36 while at the same time being configured to provide a working distance that enables insertion of suitable viewing optics (not shown), including a beam splitter for example, operative to image target region 26.

Reference is now made to FIG. 14 which is a simplified side view illustration of an image acquisition assembly 23 configured in accordance with an embodiment of the invention. Image acquisition assembly 23 includes a camera 131 acquiring an image of target region 26 along an optical axis 132. In the embodiment shown in FIG. 14, axis 132 is generally perpendicular to target region 26, although this need not be the case. Images from camera 131 are provided to an image processor 133 for suitable processing and defect detection, for example detection of defects in electrical circuits. In an embodiment of the invention, as seen in FIG. 14, the viewing path of camera 131 is folded, using at least one mirror 135 or other suitable periscopic optics, for example.

A plurality of illumination units 24 and at least one on-axis illumination unit 124 illuminate target area 26 viewed by camera 131. Illumination units 24 each employ a concentrator 36, illustrated and described with reference to FIGS. 2-7 in accordance with an embodiment of the invention, for example. On-axis illumination unit 124 employs a concentrator 137, configured in accordance with another embodiment of the invention, which shares some of the operative and structural features of concentrator 36.

As seen in FIG. 14, concentrators 36 are aligned side-by-side to illuminate a target region 26. A gap 142 is provided between two of concentrators 36 to enable illumination along axis 132 as well as viewing of target area 26 by camera 131 therealong. Illumination generally filling gap 142 is provided by on-axis illumination unit 124 and employs a concentrator 137 configured in accordance with another embodiment of the invention. Illumination from concentrator 137 passes through a beam splitter 150, suitably a partially reflective slab of light transmissive material, which in accordance with an embodiment of the invention as seen in FIG. 14, additionally is part of the periscopic optics folding the viewing path of camera 131.

Thus, as seen in FIG. 14, illumination unit 124 illuminates provides illumination close to optical axis 132, within an angle that slightly overfills gap 142. For angles that are farther offset from optical axis 132, target region 26 is illuminated by illumination provided by at least one illumination unit 24, it being noted that illumination units 24 may be selectably operated to govern the extent of off-optical-axis illumination illuminating target region 26 as required to meet the demands of different imaging applications.

Thus, in accordance with an embodiment of the invention, different combinations of illumination are provided by one or more illumination units 24 and 124, as required for a given imaging application. Illumination combinations include, for example without limitation:

Simultaneous operation of illumination unit 124 and by all of illumination units 24 to provide illumination that includes both on-axis and off-axis illumination;

Simultaneous operation of illumination unit 124 and some of illumination units 24 to provide illumination that includes both on-axis and off-axis illumination. The number of illumination units 24 that is operated may be selected to govern the angular extent of off-axis illumination in addition to on-axis illumination;

Operation of illumination unit 124 only, without operation of any of illumination units 24, thereby illuminating target region 26 with illumination relatively close to the optical axis 132;

Operation of one or more illumination units 24 without operation of illumination unit 124, thereby illuminating target region 26 with illumination set off from the optical axis 132, without illuminating target region 26 with illumination close to the optical axis 132.

In accordance with an embodiment of the invention, on-axis illumination is provided by an illumination unit 124 that includes a concentrator 137. Although illumination unit 124 is shown as providing on-axis illumination, it may be suitable for any application requiring concentration of light along a linear target region. Light is provided by a light source 134 comprising an extended source, typically a compact extended source such as a LED, for example. Light enters concentrator 137 through a curved entry surface 146 reflects off an aspheric reflective surface 142, for example by total internal reflection, although surface 142 may be provided with a suitable reflective coating to enhance reflectivity, and subsequently exits through exit surface 152.

Light source 134 and entry surface are configured so that light from light source 134 enters through surface 146 at an angle generally normal thereto, is reflected by surface 142 and subsequently exits concentrator 137 through exit surface 152 at an angle generally normal thereto. It is noted that because light source 134 is a compact extended source, and not a perfect point source, not all light emitted therefrom will impinge on surfaces 146 and 152 at angles precisely normal to the respective surface; small deviations from the normal can be expected.

Although the optical designs described hereinabove with respect to 2-8 are characterized by symmetry about a central plane, the principles of the present invention may also be applied in producing non-symmetrical optical concentrators, for example as described with reference to FIG. 14, although other non-symmetrical designs sharing design concepts described herein may also be employed.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

APPENDIX—EXEMPLARY DESIGN PARAMETERS

Table A1 below lists the coordinate profile of reflecting surfaces 42 and 44 (in mm), as shown in FIG. 3. The origin of the coordinates is taken to be the location of light source 34 in the figure.

TABLE A1

| Profile Of Aspheric Reflecting Surfaces | |
|---|---|
| Y | Z |
| 6.946 | 16.108 |
| 6.921 | 15.873 |
| 6.897 | 15.643 |
| 6.872 | 15.414 |
| 6.846 | 15.184 |

TABLE A1-continued

Profile Of Aspheric Reflecting Surfaces

| Y | Z |
|---|---|
| 6.820 | 14.955 |
| 6.793 | 14.725 |
| 6.765 | 14.496 |
| 6.737 | 14.266 |
| 6.708 | 14.037 |
| 6.679 | 13.807 |
| 6.648 | 13.577 |
| 6.618 | 13.348 |
| 6.586 | 13.118 |
| 6.554 | 12.889 |
| 6.521 | 12.659 |
| 6.488 | 12.430 |
| 6.454 | 12.200 |
| 6.419 | 11.971 |
| 6.383 | 11.741 |
| 6.347 | 11.512 |
| 6.310 | 11.282 |
| 6.272 | 11.052 |
| 6.233 | 10.823 |
| 6.194 | 10.593 |
| 6.153 | 10.364 |
| 6.112 | 10.134 |
| 6.070 | 9.905 |
| 6.027 | 9.675 |
| 5.984 | 9.446 |
| 5.939 | 9.216 |
| 5.893 | 8.986 |
| 5.847 | 8.757 |
| 5.799 | 8.527 |
| 5.751 | 8.298 |
| 5.702 | 8.068 |
| 5.651 | 7.839 |
| 5.599 | 7.609 |
| 5.547 | 7.380 |
| 5.493 | 7.150 |
| 5.438 | 6.921 |
| 5.382 | 6.691 |
| 5.324 | 6.461 |
| 5.266 | 6.232 |
| 5.205 | 6.002 |
| 5.144 | 5.773 |
| 5.081 | 5.543 |
| 5.017 | 5.314 |
| 4.951 | 5.084 |
| 4.883 | 4.855 |
| 4.814 | 4.625 |
| 4.743 | 4.395 |
| 4.671 | 4.166 |
| 4.596 | 3.936 |
| 4.519 | 3.707 |
| 4.440 | 3.477 |
| 4.359 | 3.248 |
| 4.276 | 3.018 |
| 4.190 | 2.789 |
| 4.101 | 2.559 |
| 4.009 | 2.330 |
| 3.915 | 2.100 |
| 3.817 | 1.870 |
| 3.715 | 1.641 |
| 3.609 | 1.411 |
| 3.499 | 1.182 |
| 3.385 | 0.952 |
| 3.264 | 0.723 |
| 3.138 | 0.493 |
| 3.005 | 0.264 |
| 2.863 | 0.034 |
| 2.841 | 0.000 |

The invention claimed is:

1. An optical element comprising:

a unitary, non-circularly-symmetrical, piece of optically-transmissive material, which has at least lateral regions and a central region for concentrating light from a light source onto a linear target region, wherein the central region is disposed between the lateral regions;

wherein at least one of lateral surfaces of the lateral regions and an exit surface of the central region, is curved, and wherein a first portion of the light is concentrated onto the linear target region by reflection from the lateral surfaces, while a second portion of the light is focused in a sagittal plane by refraction at the exit surface of the central region; and wherein light reflected from the lateral surfaces is not refracted in the sagittal plane at an exit surface of the optical element.

2. The optical element according to claim 1, wherein the light is reflected from the lateral surfaces by total internal reflection.

3. The optical element according to claim 1, wherein the lateral surfaces and the exit surface of the central region are curved, and wherein the lateral surfaces have aspheric profiles of curvature.

4. The optical element according to claim 1, wherein the piece of optically-transmissive material has a plane of symmetry that passes through the light source and the target region.

5. The optical element according to claim 4, wherein the second portion of the light comprises second rays emitted from the light source into a low range of sagittal angles relative to the plane of symmetry, while the first portion of the light comprises first rays emitted from the light source into a high range of sagittal angles relative to the plane of symmetry.

6. The optical element according to claim 5, wherein the high range adjoins the low range, such that the low and high ranges of sagittal angles together comprise at least 130° in a sagittal plane of the optical element.

7. The optical element according to claim 6, wherein the low and high ranges of sagittal angles together comprise nearly 180° in a sagittal plane of the optical element.

8. The optical element according to claim 6, wherein the low and high ranges of sagittal angles together comprise 270° in the sagittal plane of the optical element.

9. The optical element according to claim 6, wherein the low and high ranges of sagittal angles together comprise 360° in the sagittal plane of the optical element.

10. The optical element according to claim 5, wherein the light source is substantially linear and wherein the second rays emitted by each point along the light source into the low range of sagittal angles are substantially focused onto a curved illumination region within the plane of symmetry.

11. The optical element according to claim 10, wherein the first rays, emitted into the high range of sagittal angles are substantially focused onto a linear illumination region within the plane of symmetry, and wherein the curved illumination region formed by the second rays overlaps with linear illumination region formed by the first rays.

12. The optical element according to claim 5, wherein the light source is substantially linear and wherein the first rays, emitted into the high range of sagittal angles are substantially focused onto a linear illumination region within the plane of symmetry.

13. The optical element of claim 4, wherein all external surfaces of the optical element are draft angles with respect to opposing directions in the plane of symmetry.

14. The optical element according to claim 1, wherein the lateral surfaces are lateral side surfaces and the piece of optically-transmissive material further has lateral entry surfaces, through which the first portion of the light enters the piece, and a central collecting surface, adjoining the lateral entry surfaces, through which the second portion of the light enters the piece.

15. The optical element according to claim 14, wherein the piece of optically transmissive material further has lateral exit surfaces, through which the first portion of the light exits the piece, and wherein the lateral entry surfaces and the lateral exit surfaces are configured so as to minimize tangential field curvature.

16. The optical element according to claim 14, wherein the central collecting surface and the exit surface of the central region comprise curved surfaces.

17. The optical element according to claim 14, wherein the lateral entry surfaces and the central collecting surface together define a cavity, which contains the light source.

18. The optical element according to claim 1, wherein said unitary piece of optically-transmissive material additionally includes a pair of planar end surfaces disposed perpendicularly to the lateral surfaces and the exit surface of the central region, said planar end surfaces being configured to reflect light from said light source onto said linear target region.

19. The optical element of claim 1, wherein marginal rays of light incident on the target surface are incident from the outermost edges of exit surfaces of the lateral regions.

20. The optical element according to claim 1, wherein the first portion of the light enters the optical element through lateral entry surfaces, and the first portion of the light is not refracted in the sagittal plane at the lateral entry surfaces.

21. An optical element comprising:
a piece of optically-transmissive material, which has at least lateral surfaces and a central exit surface for concentrating light from a light source onto a linear target region, such that a first portion of the light is concentrated onto the target region by internal reflection from the lateral surfaces, while a second portion of the light is focused in a sagittal plane onto the linear target region by refraction at the central exit surface,
wherein the piece of optically-transmissive material has an entry surface, through which the first portion of the light enters the piece before reflecting from the lateral surfaces, and a collecting surface, adjoining the entry surface, through which the second portion of the light enters the piece before being refracted in the sagittal plane at the central exit surface, said entry surface being arranged relative to said light source to receive light emitted by said light source at angle generally perpendicular to a tangent thereof in the sagittal plane; and
wherein, after being reflected from the lateral surfaces, the first portion of the light is incident on an exit surface at angles generally perpendicular to a tangent of the exit surface in the sagittal plane.

22. An assembly for concentrating light from first and second light sources, the assembly comprising:
a first optical element, which comprises a first unitary, non-circularly-symmetrical piece of optically-transmissive material, which has at least lateral surfaces and a central exit surface for concentrating the light from the first light source onto a linear target region over a first range of sagittal angles, such that a first portion of the light from the first light source is focused by internal reflection from the lateral surfaces, while a second portion of the light from the first light source is focused in a sagittal plane by refraction at the central exit surface,
wherein the first portion of the light from the first light source is not refracted in the sagittal plane at an exit surface of the first optical element; and a second optical element, which comprises a second unitary, non-circularly-symmetrical piece of optically-transmissive material, which has at least lateral surfaces and a central exit surface for concentrating the light from the second light source onto the linear target region over a second range of sagittal angles, such that a first portion of the light from the second light source is focused by internal reflection from the lateral surfaces, while a second portion of the light from the second light source is focused in a sagittal plane by refraction at the central exit surface;
wherein the first portion of the light from the second light source is not refracted in the sagittal plane at an exit surface of the second optical element.

23. An illumination unit, comprising:
a light source; and
an optical element comprising a unitary, non-circularly-symmetrical piece of optically-transmissive material, which has at least lateral surfaces and a central exit surface for concentrating light from the light source onto a linear target region, such that at least one of the lateral surfaces and the central exit surface is curved, and such that a first portion of the light is focused onto the target region by internal reflection from the lateral surfaces, while a second portion of the light is focused in a sagittal plane onto the target region by refraction at the central exit surface;
wherein the first portion of the light is not refracted in the sagittal plane at an exit surface of the optical element.

24. The illumination unit according to claim 23, wherein the light source comprises an array of light-emitting diodes having a longitudinal axis parallel to the linear target region.

25. A system for optical inspection of an object, comprising:
an illumination unit, which comprises:
a plurality of light sources; and
an optical element comprising a unitary, non-circularly-symmetrical piece of optically-transmissive material for illuminating a target region, which has at least lateral surfaces and a central exit surface for concentrating light from the plurality of light source onto a linear target region on the object, such that at least one of the lateral surfaces and the central exit surface is curved, and such that a first portion of the light is focused by internal reflection from the lateral surfaces, while a second portion of the light is focused in a sagittal plane by refraction at the central exit surface,
wherein the first portion of the light is not refracted in the sagittal plane at an exit surface of the optical element;
a linear detector array, which is configured to receive the light reflected from the target region and to generate an output signal responsively to the received light; and
a processor, which is coupled the linear detector array to process the output signal so as to assess the object.

26. The system according to claim 25, and comprising a motion assembly, which is couples to scan the linear target region over the object.

27. A method for producing an optical element, the method comprising molding a unitary, non-circularly-symmetrical piece of optically-transmissive material so as to define at least lateral surfaces and a central exit surface for concentrating light from a light source onto a linear target region, such that at least one of the lateral surfaces and the central exit surface is curved, and such that a first portion of the light is focused by internal reflection from the lateral surfaces and is not refracted in a sagittal plane at an exit surface of the element, while a second portion of the light is focused in the sagittal plane by refraction at the central exit surface.

28. An illumination assembly, comprising:
  a plurality of light sources; and a non-circularly-symmetrical piece of optically-transmissive material, having:
    a curved entry surface for receiving light from ones of said plurality of light sources, said plurality of light sources and said curved entry surface being configured and arranged such that light from said ones of said plurality of light source impinges on said curved entry surface in directions that are generally normal to a tangent of said curved entry surface in a sagittal plane;
    a lateral surface for reflecting light received from said light source through said curved entry surface onto a linear target region; and
    a curved exit surface receiving light received from said lateral surface, said curved exit surface being configured and arranged relative to said lateral surface such that light reflected from said lateral surface impinges on said curved exit surface in directions that are normal to a tangent of said curved exit surface in a sagittal plane;
  wherein light reflected by lateral surface is concentrated onto said target region.

29. An optical element comprising a unitary piece of optically-transmissive material, symmetric about a plane of symmetry, for directing light from a light source onto a target region, the piece having:
  symmetrically-disposed lateral regions, each having:
    a lateral surface, wherein light from the light source is focused by reflection from the lateral surfaces, and
    an exit surface which transmits the light reflected from the lateral surface toward the target region without refraction in a sagittal plane at the exit surface; and
  a central region, bisected by the plane of symmetry and disposed between the lateral regions, having a light-incident surface, onto which light is incident from a the light source, and an exit surface which focuses light in the sagittal plane from the light-incident surface toward the target region;
  wherein the target region is a line along the plane of symmetry.

30. An optical element comprising;
  a unitary piece of optically transmissive material, having lateral regions and a central region disposed between the lateral regions, symmetric about a plane of symmetry, for directing light from a light source onto a target region;
  wherein light from the light source enters the optical element through at least one entry surface and the light from the light source is not refracted in a sagittal plane at the at least one entry surface;
  wherein a first portion of light from the light source is focused by reflection from lateral surfaces of the lateral regions and is output through lateral exit surfaces, wherein the first portion of light is not refracted in a sagittal plane at the lateral exit surfaces;
  wherein a second portion of light from the light source is focused by refraction in the sagittal plane at an exit surface of the central region;
  wherein light output from the exit surfaces of the lateral regions and from the exit surface of the central region forms a continuous range of angles in the sagittal plane, such that marginal rays of light incident on the target region are incident from outermost edges of the lateral exit surfaces; and
  wherein all external surfaces of the optical element are draft angles with respect to opposing directions in the plane of symmetry.

* * * * *